US00PP37218P2

(12) United States Plant Patent
Deng

(10) Patent No.: US PP37,218 P2
(45) Date of Patent: Jan. 13, 2026

(54) ***CALADIUM* PLANT NAMED 'UF-15-131'**

(50) Latin Name: ***Caladium* x *hortulanum***
Varietal Denomination: UF-15-131

(71) Applicant: Florida Foundation Seed Producers, Inc., Marianna, FL (US)

(72) Inventor: Zhanao Deng, Riverview, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 19/287,954

(22) Filed: Aug. 1, 2025

Related U.S. Application Data

(60) Provisional application No. 63/715,701, filed on Nov. 4, 2024.

(51) Int. Cl.
*A01H 5/12* (2018.01)
*A01H 5/06* (2018.01)
*A01H 6/00* (2018.01)

(52) U.S. Cl.
USPC ..... Plt./373
CPC ..... *A01H 6/00* (2018.05); *A01H 5/06* (2013.01); *A01H 5/12* (2013.01)

(58) Field of Classification Search
USPC ..... Plt./263.1, 373
See application file for complete search history.

(56) References Cited

U.S. PATENT DOCUMENTS

PP26,833 P2 * 6/2016 Deng ..... A01H 6/10
Plt./373

* cited by examiner

*Primary Examiner* — Karen M Redden
(74) *Attorney, Agent, or Firm* — James R. Holm

(57) ABSTRACT

A new and distinct cultivar of *Caladium* plant named 'UF-15-131', characterized by its dense growth habit that is suitable for growing in 4-inch or larger in diameter containers; heart-shaped and peltate leaves that have green, greyed-green and yellow-green colored midribs and primary veins; green-white, white, yellow-green and greyed green interveinal areas with numerous deep red-purple spots or blotches across the leaf blade on the upper surface of fully developed leaves; moderately rugose leaf blades and moderately ruffled leaf margins; tolerance to sunburns; excellent leaf health in full sun; moderate resistance to Fusarium tuber rot caused by *Fusarium solani*; moderate resistance to *Pythium* root rot caused by *Pythium myriotylum*; and moderately resistant to resistant to root-knot nematodes *Meloidogyne javanica* and *Meloidogyne arenaria.*

7 Drawing Sheets

CROSS-REFERENCE TO RELATED APPLICATIONS

This Application is related to and claims the benefit of U.S. Provisional Patent Application Ser. No. 63/715,701 filed on Nov. 4, 2024, entitled *CALADIUM* CULTIVARS, the entirety of which is incorporated herein by reference.

Genus and species: *Caladium* x *hortulanum.*

Cultivar denomination: 'UF-15-131'.

STATEMENT REGARDING PRIOR DISCLOSURES BY THE INVENTORS

The Applicants assert that no publications or advertisements relating to sales, offers for sale, or public distribution occurred more than one year prior to the effective filing date of this application. Any information about the claimed plant would have been obtained from a direct or indirect disclosure from the Inventor. The Applicants claim a prior art exemption under 35 U.S.C. 102(b)(1) for disclosures and/or sales that fall within a one-year grace period prior to the effective filing date of this application.

BACKGROUND OF THE NEW CULTIVAR

The present invention relates to a new and distinct cultivar of *Caladium*, botanically known as *Caladium* x *hortulanum*, and hereinafter referred to by the name 'UF-15-131'. *Caladium* plants are tuberous-rooted plants and typically have attractive heart-shaped or arrow-shaped leaves on long stalks rising directly from the tubers. Foliage may grow in a variety of colors and variegation patterns, and many species have been developed for aesthetic coloration, good container and landscape growth, drought tolerance, pest resistance, and other desirable characteristics.

SUMMARY OF THE INVENTION

The new *Caladium* cultivar 'UF-15-131' has not been observed under all possible environmental conditions. The phenotype of the new cultivar may vary with variations in environment and cultural practices such as temperature, light intensity, fertilization, irrigation, and application of plant growth regulators without any change in genotype.

The objective of the breeding program that produced the present cultivar was to develop cultivars that have novel foliar characteristics, produce multiple brightly colored leaves, have good tuber yield potential, perform well in containers and the landscape, have resistance to tuber and root diseases, and have tolerance to sunburns. The present *Caladium* cultivar originated from a cross-pollination made in 2012 in Wimauma, Florida between the *Caladium* x *hortulanum* breeding line 'UF 317' (unpatented), as the female or seed parent, and the *Caladium* x *hortulanum* cultivar 'Florida Fantasy' (unpatented), as the male or pollen parent. The new *Caladium* cultivar was discovered and selected by the inventor in Wimauma, Florida in the spring of 2014 as a single plant within the progeny of the stated cross-pollination.

Asexual reproduction of the new cultivar 'UF-15-131' by tuber divisions in a controlled environment has been performed annually in Wimauma, Florida since April 2014. The unique features of this new *Caladium* cultivar are stable and reproduced true to type in successive generations of asexual reproduction by tuber divisions.

The new cultivar 'UF-15-131' has not been observed under all possible environmental conditions. The phenotype may vary somewhat with variations in environment such as temperature and light intensity, without, however, any variance in genotype.

The following traits have been repeatedly observed and are determined to be the unique characteristics of 'UF-15-131'. These characteristics in combination distinguish 'UF-15-131' as a new and distinct cultivar of *Caladium:*

1. Dense growth habit suitable for growing in 4-inch or more in diameter containers;
2. Heart shaped and peltate leaves with green, greyed-green and yellow-green colored midribs and primary veins;
3. Green-white, white, yellow-green and greyed green interveinal areas with numerous deep red-purple spots or blotches across the leaf blade on the upper surface of fully developed leaves;
4. Moderately rugose leaf blades and moderately ruffled leaf margins;
5. Plants with tolerance to leaf sunburns when grown in open fields;
6. Moderately resistant to *Fusarium* tuber rot caused by *Fusarium solani;*
7. Resistant to *Pythium* root rot caused by *Pythium myriotylum*; and
8. Moderately resistant to resistant to root-knot nematode species *Meloidogyne javanica* and *Meloidogyne arenaria.*

Plant of the new *Caladium* cultivar 'UF-15-131' differ from plants of the female parent, 'UF 317', in the following characteristics:

1. Plants of 'UF-15-131' have more leaves and are fuller than plants of *Caladium* line 'UF 317';
2. Leaves of 'UF-15-131' do not have an overtone of pink or red coloration; and
3. Plants of 'UF-15-131' produce larger and more numerous tubers.

Plants of the new *Caladium* cultivar 'UF-15-131' differ from plants of the male parent, 'Florida Fantasy', in the following characteristics:

1. Plants of 'UF-15-131' are taller than plants of 'Florida Fantasy';
2. Leaves of 'UF-15-131' have green, greyed-green and yellow-green colored midribs and primary veins, whereas leaves of 'Florida Fantasy' have red colored midribs and reddish white colored primary veins; and
3. Leaves of 'UF-15-131' have numerous red-purple spots across the leaf blade, whereas leaves of 'Florida Fantasy' lack any spots or blotches.

Plants of 'UF-15-131' can also be compared to plants of the commercial *Caladium* cultivar 'Cranberry Star' (U.S. Plant Pat. No. 20,792). In side-by-side comparisons conducted in Wimauma, FL, plants of 'UF-15-131' differed from plants of 'Cranberry Star' in leaf color, quantity of leaf spots, petiole color, and tolerance to sunburns. 'Cranberry Star' had fewer leaves and fewer leaf spots. Leaf spots on 'Cranberry Star' were lighter in color and the petioles were greener near the attachment to the leaf blade. 'UF-15-131' had greater tolerance to sunburns, whereas 'Cranberry Star' was more susceptible to sunburn damage.

Plants of 'UF-15-131' can also be compared to plants of the commercial *Caladium* cultivar 'UF-85-5' (U.S. Plant Pat. No. 24,681, commercial name "Strawberry Star"). In side-by-side comparisons conducted in Wimauma, FL, plants of 'UF-15-131' differed primarily from plants of 'UF-85-5' in leaf color, quantity of leaf spots, leaf blade rugosity, leaf margin ruffling, and petiole color. Leaves of 'UF-85-5' had fewer spots, leaf blades were flat and rarely rugose, leaf margins were only slightly ruffled or waved, and petioles were yellow-green.

DESCRIPTION OF THE FIGURES

The accompanying photographs (as shown in FIGS. 1-7) illustrate the overall appearance of the new *Caladium* cultivar 'UF-15-131'. These photographs show the colors as true as can be reasonably obtained in colored reproductions of this type. Colors in the photographs may differ slightly from the color values cited in the detailed botanical description, which accurately describes the colors of the new *Caladium* cultivar.

DETAILED BOTANICAL DESCRIPTION OF THE CULTIVAR

Figure 1:
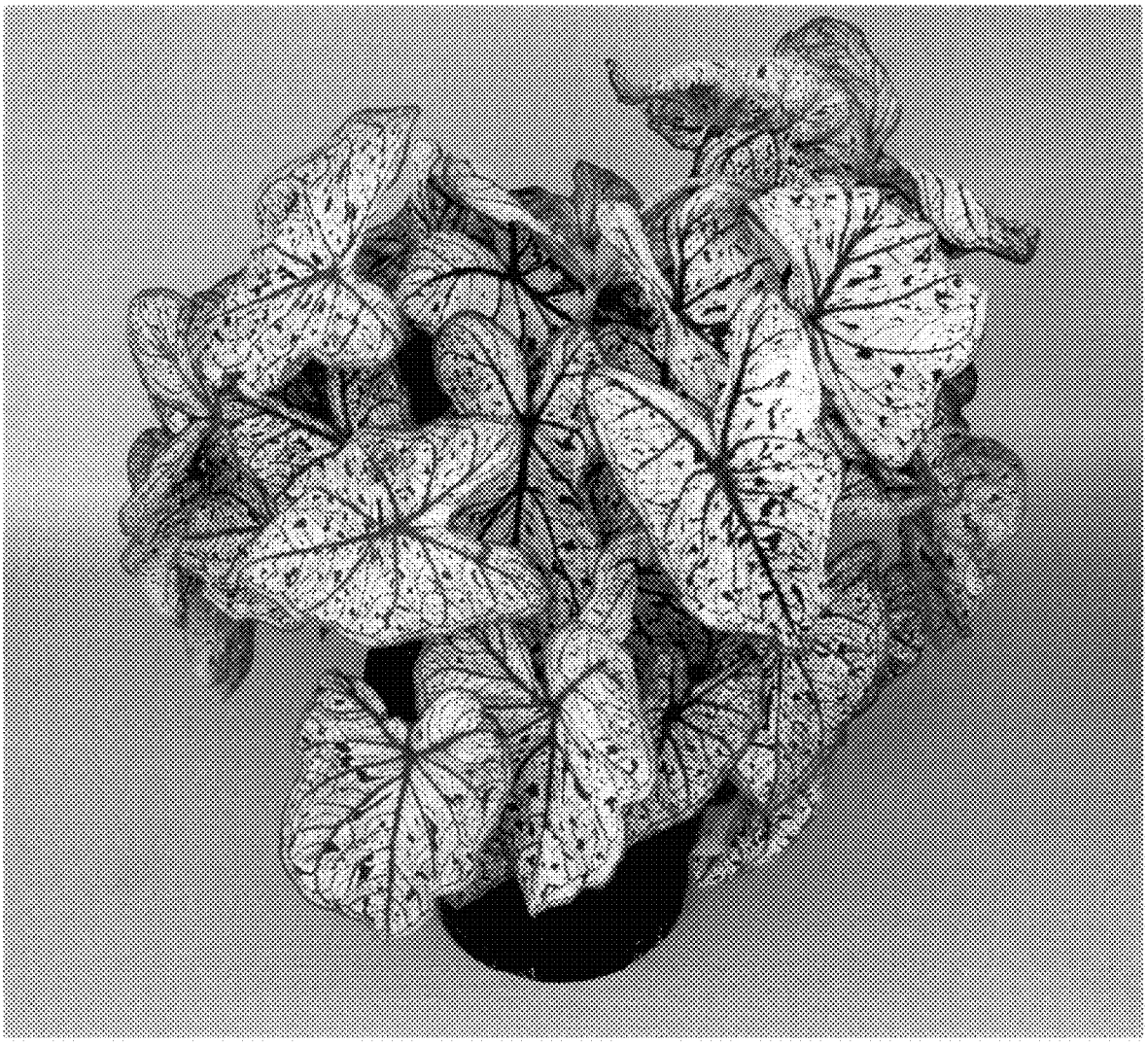
FIG. 1 shows a side perspective view of a typical plant of 'UF-15-131' grown in containers in a greenhouse.
Figure 2:
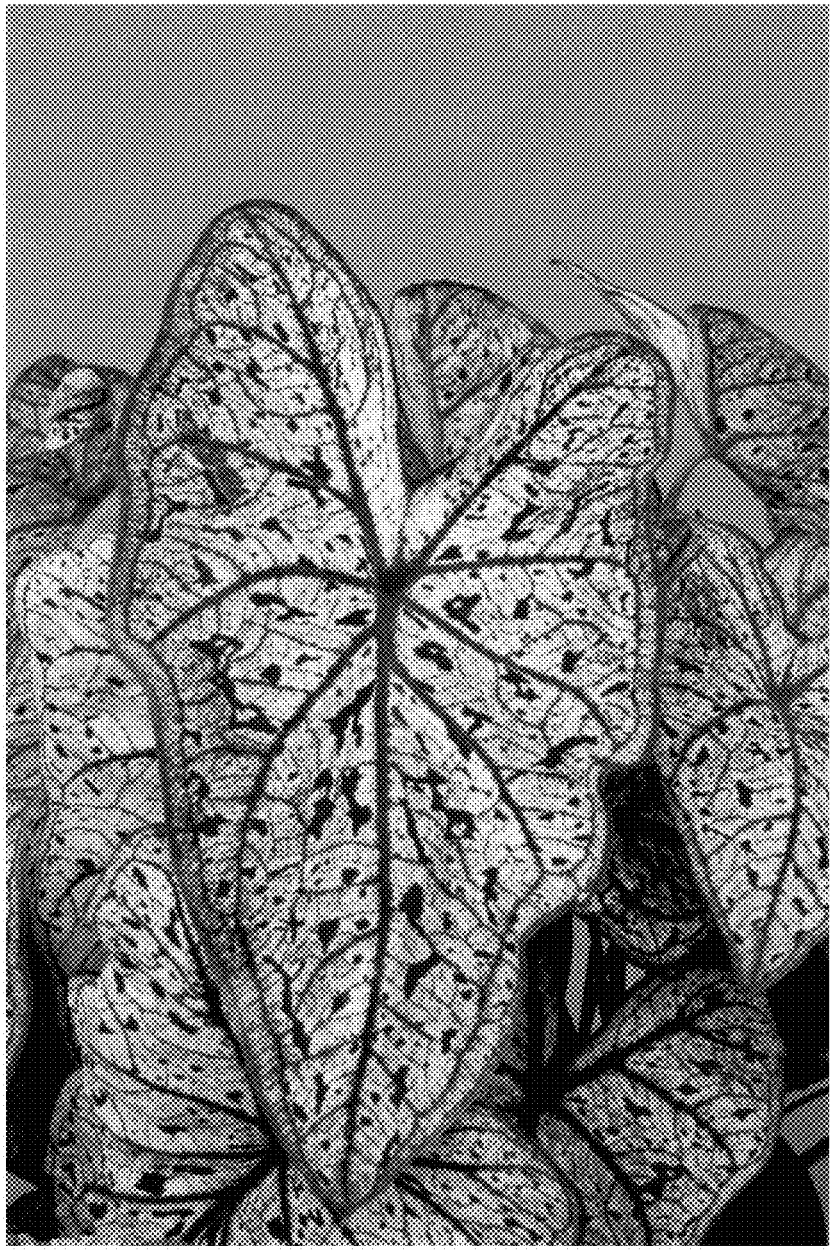
FIG. 2 shows a close up of a typical leaf of plants of 'UF-15-131' grown in containers in a greenhouse.
Figure 3:
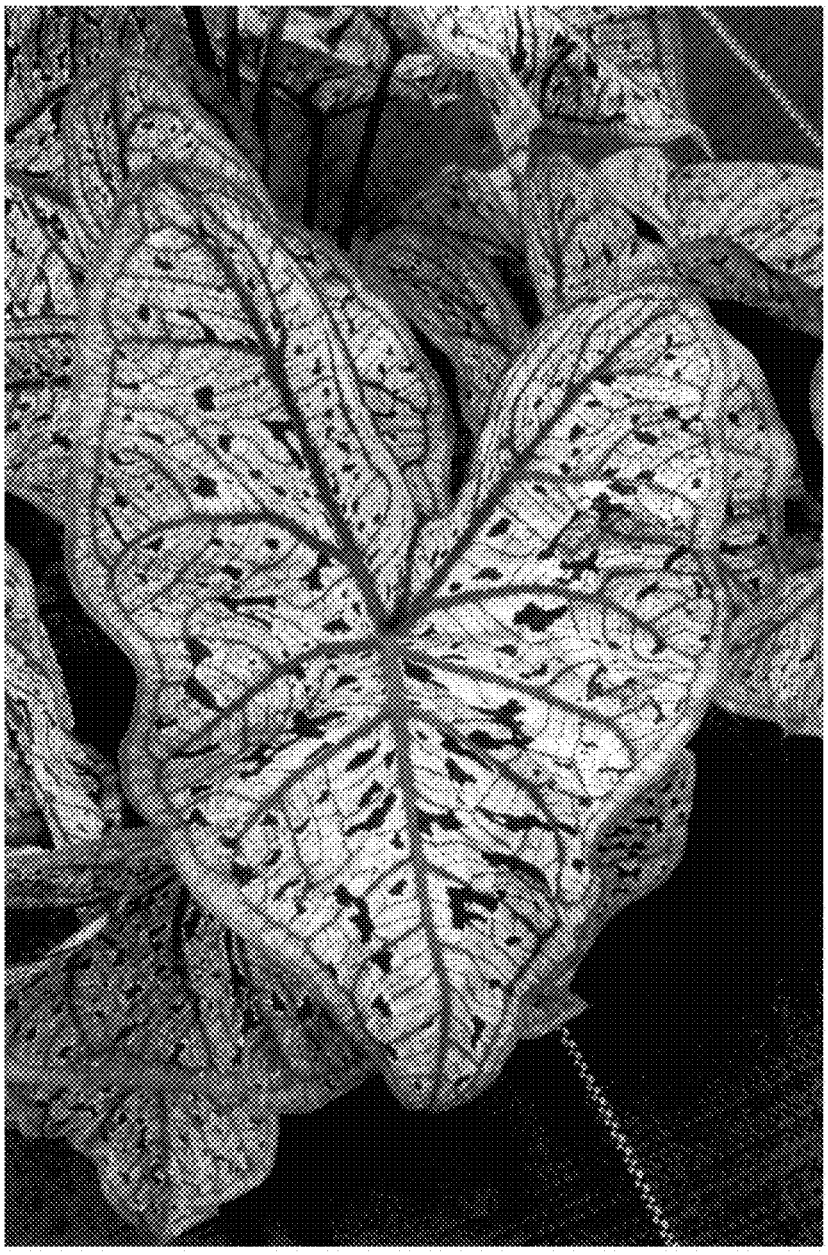
FIG. 3 shows a close up of a typical leaf of plants of 'UF-15-131' grown in a ground bed in an outdoor nursery with approximately 30% shading.
Figure 4:
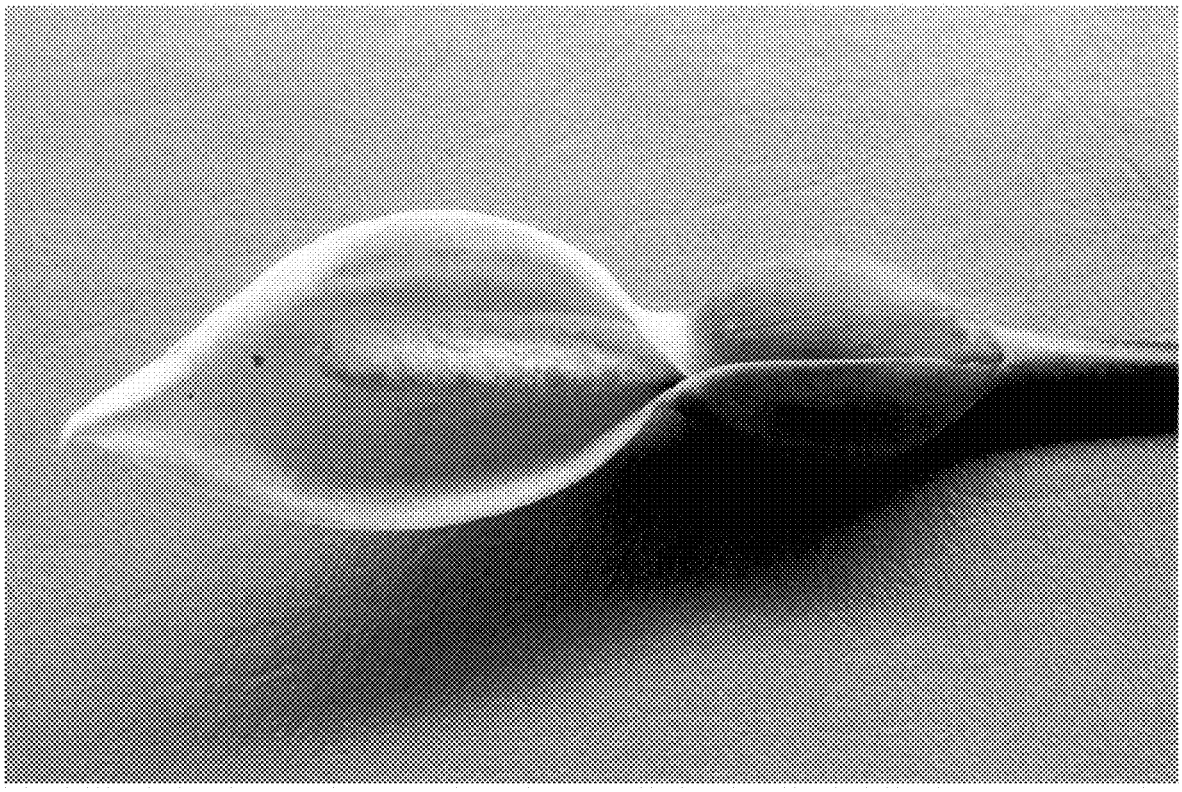
FIG. 4. shows a typical bloom observed on plants of 'UF-15-131' grown in containers in a greenhouse.
Figure 5:
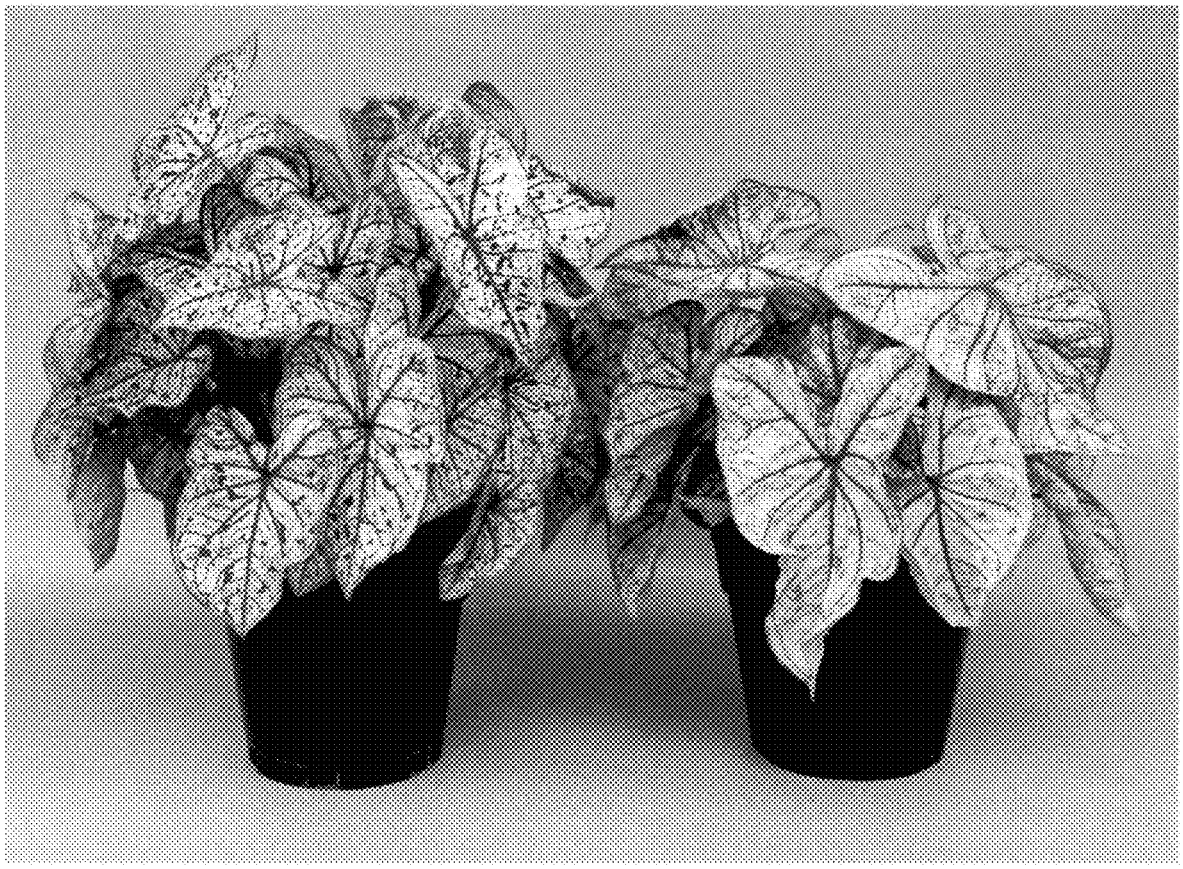
FIG. 5. shows a side perspective view of typical plants of 'UF-15-131' (left) compared to the commercial cultivar 'Cranberry Star' (right) grown in containers in a greenhouse.
Figure 6:
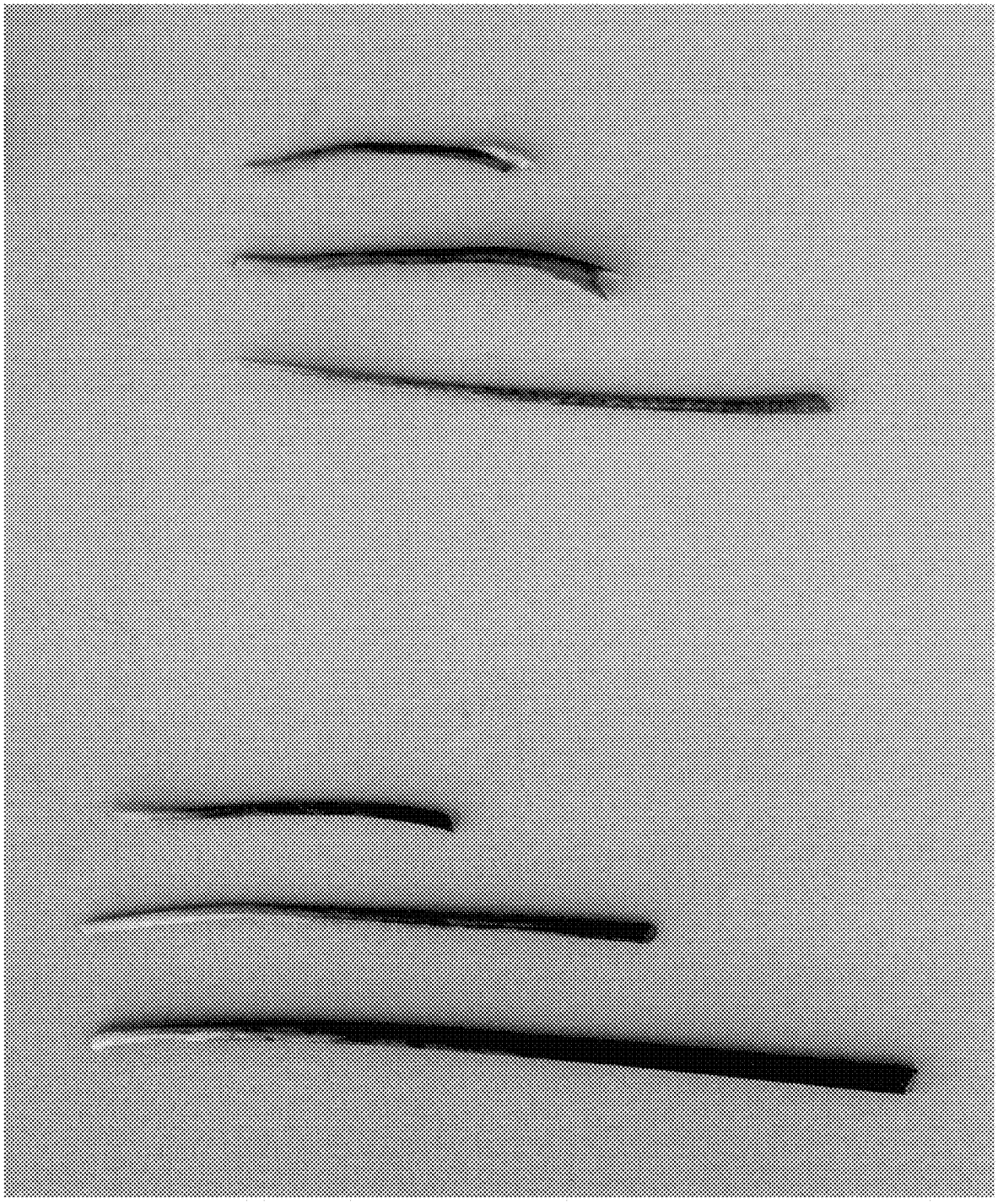
FIG. 6. shows typical petioles of plants of 'UF-15-131' (bottom three petioles) compared to the petioles of the commercial cultivar 'Cranberry Star' (top three petioles)
Figure 7:
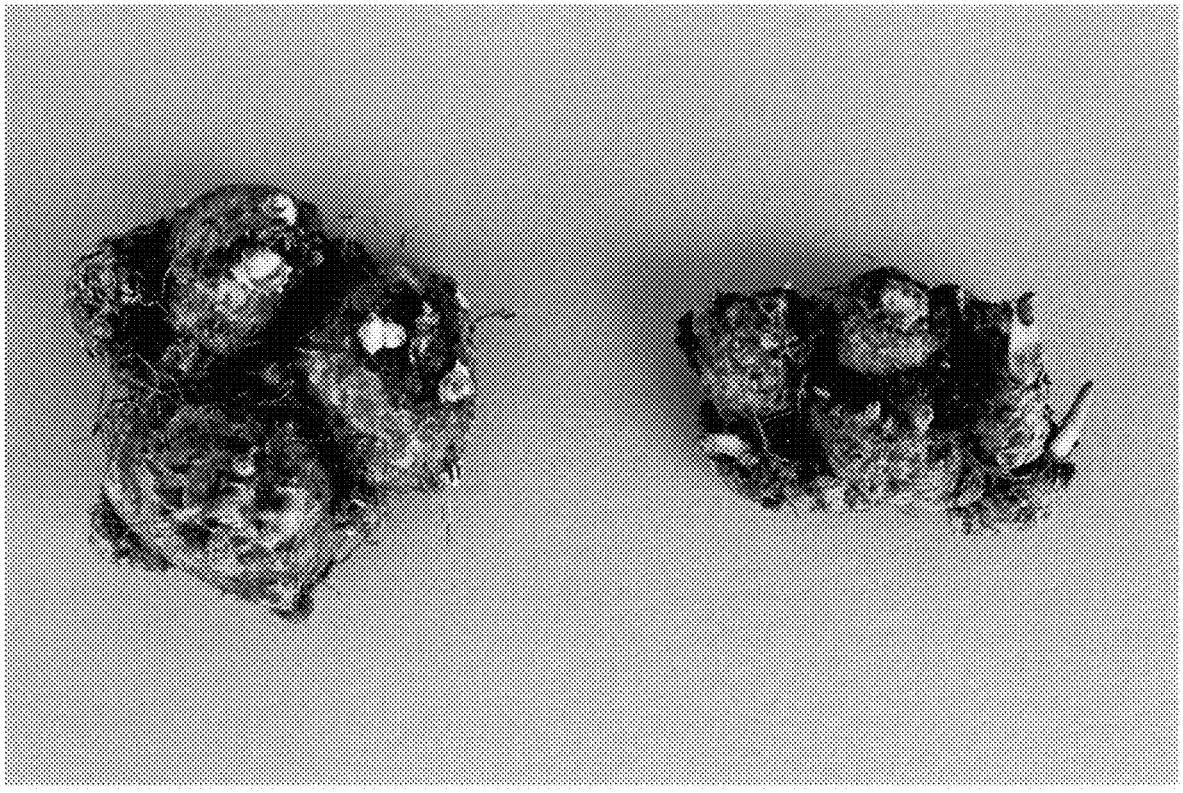
FIG. 7. shows a top view of typical tubers produced by plants of 'UF-15-131' (left) compared to tubers of the commercial cultivar 'Cranberry Star' (right).

In the following description, color references are made to The Royal Horticultural Society (R.H.S.) Colour Chart, 1986 Edition, except where general terms of ordinary dictionary significance are used.

Description of Growing Conditions

The aforementioned photographs and the following observations and measurements describe plants grown in 20-cm containers in Wimauma, Florida during the summer in a polypropylene-covered shade house and also describe plants grown in an outdoor nursery in ground beds in Wimauma, Florida during the late summer. All plants were grown under conditions and practices that approximate those generally used in commercial *Caladium* production.

During the production of the plants, day temperatures ranged from about 26° C. to 35° C., night temperatures ranged from about 18° C. to 26° C. and light levels ranged from 2400 to 3840 foot-candles in the greenhouse and 8300 foot-candles for plants grown in the outdoor nursery. Plants grown in the greenhouse were about 6 weeks old from tubers when the photographs and the detailed description were taken. Plants grown in the outdoor nursery were about 3 months old from tubers when the photographs and the detailed description were taken.

Botanical Description

Botanical classification:

*Family*.—Araceae.

*Botanical name*.—*Caladium* x *hortulanum*.

*Common name*.—*Caladium* or *Caladium*.

*Cultivar*.—'UF-15-131'.

Parentage:

*Female or seed parent*.—*Caladium* x *hortulanum* breeding line 'UF 317' (unpatented).

*Male or pollen parent*.—*Caladium* x *hortulanum* cultivar 'Florida Fantasy' (unpatented).

Propagation:

*Type*.—By tubers and by tuber divisions.

*Time to initiate roots, summer*.—About seven to ten days at 32° C.

*Time to initiate roots, winter*.—About two to three weeks at 24° C.

Tuber description:

*Number of buds on a 2.5 to 3.5 inch in diameter tuber (greenhouse-grown plants)*.—About 5 to 10 actively growing buds/shoots.

*Number of buds on a 2.5 to 3.5 inch in diameter tuber (outdoor nursery-grown plants)*.—About 5 to 10 actively growing buds/shoots.

*Height*.—4.0 to 7.0 cm.

*Diameter*.—5.0 to 9.0 cm.

*Texture*.—Thick, starchy, and hairy with fine dried roots.

*Color*.—Epidermis: 15D (yellow-orange) and 164A to 166A (greyed-orange). Interior: 14C to 15C (yellow-orange).

Root description: Dense, thick, and white fleshy roots.

Plant description:

*Type*.—Herbaceous perennial.

*Growth habit*.—Vigorous and dense growth habit with an abundance of leaves, suitable for growing in containers.

*Leaf petioles*.—Arising from tubers, mostly upright, curving outwardly with development.

*Plant height, from soil level to top of the leaf plane*.—Greenhouse grown plants: Average 39.0 cm. Outdoor nursery grown plants: Average 56.0 cm.

*Plant height, from soil level to top of the inflorescences*.—Greenhouse grown plants: Average 45.0 cm. Outdoor nursery grown plants: Inflorescences not observed on outdoor grown plants.

*Plant diameter or spread*.—Greenhouse-grown plants: Average 53.0 cm. Outdoor nursery grown plants: Average 40.0 cm.

Foliage description:

*Length*.—Greenhouse grown plants: Average 24.6 cm. Outdoor nursery grown plants: Average 31.0 cm.

*Width (flattened)*.—Greenhouse grown plants: Average 19.1 cm. Outdoor nursery grown plants: Average 18.3 cm.

*Shape*.—Ovate to cordate, peltate.

*Apex*.—Acuminate.

*Base*.—Cordate.

*Margin*.—Entire.

*Texture*.—Upper surface: Smooth, glabrous. Lower surface: Smooth, glabrous; glaucous.

*Venation pattern*.—Palmate-pinnate.

*Color, developing leaves (greenhouse grown plants)*.—Upper surface: Interveinal areas: 196D (greyed-green) and 139A (green) with an average of 158 spots and blotches of 185B (greyed-purple), spots measuring 0.2 cm to 1.9 cm in length and 0.1 cm to 0.5 cm in width. Borders and margins: 137A and 139A (green) with a thin line of 59A and 60B (red-purple) on the extreme edge between the upper and lower leaf surface. Basal notch: 59A and 60B (red-purple). Venation: Mid rib: 136A and 137A (green). Primary veins: 133A and 139A (green). Lower surface: Interveinal areas: 138A (green) or 191A (greyed-green) with an average of 168 spots and blotches of 184B and 185B (greyed- purple), spots measuring 0.1 cm to 1.3 cm in length and 0.1 cm to 0.8 cm in width. Borders and margins: 191A (greyed-green) or 138B (green); width of margin coloration is 1.5 mm. Venation: Midrib: 194B (greyed-green) or 137B (green). Primary veins: 136B and 137A (green).

*Color, fully expanded leaves (greenhouse grown plants)*.—Upper surface: Interveinal areas: 157C and 157D (green-white) and 193B and 193C (greyed-green) with 157C, 157D, 193B, 193C and 193D flanking the midrib and primary veins and then transitioning to 145B, 145C, and 145D (yellow-green) or 157B, 157C and 157D outward towards the leaf margin; an average of 228 spots and blotches of 46A (red), spots measuring 0.2 cm to 2.0 cm in length and 0.1 cm to 0.7 cm in width. Borders and margins: 146A (yellow-green) or 139A (green) with a thin line of 60B (red-purple) on the extreme edge between the upper and lower leaf surfaces; width of margin coloration is 2.7 mm. Basal notch: 60B (red-purple). Venation: Midrib: 132A and 139A (green). Primary veins: 139A (green). Lower surface: Interveinal areas: 194D (greyed-green) with an average of 221 spots and blotches of 46A and 60A (red), spots measuring 0.2 cm to 2.2 cm in length and 0.1 cm to 0.7 cm in width. Border and margins: 138A (green); width of margin coloration is 2.5 mm. Venation: Midrib: 138B (green) and 147B (yellow-green). Primary veins: 138B (green) and 147C (yellow-green).

*Color, developing leaves (outdoor nursery grown plants)*.—Upper surface: Interveinal areas: 155A (white) and 144A (yellow green) with an average of 184 spots and blotches of 59C (red-purple). Border and margins: 144A (yellow-green) with a thin line of 60B (red-purple). Venation: Midrib: 141A and 143A (green). Primary veins: 141A (green). Lower surface: Interveinal areas: 138B (green) with spots and blotches of 184B (greyed-purple). Border and margins: 138B (green). Venation: Midrib: 157A (green-white). Primary veins: 191A (greyed-green).

*Color, fully expanded leaves* (*outdoor nursery grown plants*).—Upper surface: Interveinal areas: 155B (white) and 144A (yellow-green) with an average of 241 spots and blotches of 59B (red-purple), spots measuring 0.3 cm to 2.5 cm in length and 0.1 cm to 1.1 cm in width. Border and margins: 139A (green) with a thin line of 60B (red-purple); width of margin coloration is up to 2.5 mm. Venation (midrib and primary veins): 135A (green). Lower surface: Interveinal areas: 138B (green) with spots and blotches of 46A (purple). Border and margins: 137C (green) with an extremely thin edge of 60B (red-purple) between the upper and lower leaf surfaces. Venation: Midrib: 148C (yellow-green). Primary veins: 138B (green).

*Petiole*.—Aspect: Mostly erect, curving outwardly with development. Length: Greenhouse grown plants: Average 29.9 cm. Outdoor nursery grown plants: Average 49.2 cm. Diameter, distal: Greenhouse grown plants: Average 4.8 mm. Outdoor nursery grown plants: Average 5.3 mm. Greenhouse grown plants: Average 8.2 mm. Outdoor nursery grown plants: Average 8.3 mm. Strength: Strong and flexible. Color: Diameter, proximal: Greenhouse grown plants: 202A (black) or 200A (brown) at the proximal end, turning 197B (greyed-green) at the distal end. Outdoor nursery grown plants: 200A (brown) and 202A (black), with streaks of 201A (grey) or 145B (yellow-green) near the distal end. Wing length: Greenhouse grown plants: Average 7.4 cm. Outdoor nursery grown plants: Average 7.0 cm. Wing diameter: Greenhouse grown plants: Average 10.6 mm. Outdoor nursery grown plants: Average 12.6 mm. Wing color: Greenhouse grown plants: 200A (brown) and 159C (orange-white) and streaked with 200A (brown) and 202A (black). Outdoor nursery grown plants: 36D (red) with streaks of 200A (brown).

Inflorescence description: Only observed on greenhouse-grown plants.

*Arrangement*.—Upright hooded spathes surrounding a columnar spadix borne on a tall upright scape. Spadix with sessile, simple female and male flowers separated into two zones: female flowers arranged on the lower one-third of the spadix, male flowers arranged on the upper two-thirds of the spadix. Sterile flowers develop between female and male flower zones; near this area, the spathe constricts surrounding the female flowers.

*Fragrance*.—None detected.

*Natural flowering season*.—'UF-15-131' typically flowers during the spring or early summer in central Florida; flowers develop about seven weeks after growth commences and inflorescences last about three days before fading, inflorescences are persistent.

*Spathe*.—Length: Average 11.9 cm. Width, distal: 2.6 cm. Width, proximal: 2.0 cm. Shape: Ovate to somewhat obovate. Apex: Acute to acuminate. Base: Tapering. Margin: Entire. Texture (upper and lower surfaces): Smooth, glabrous. Color: Front surface: Upper two-thirds: 194D (greyed-green) or 150C (yellow-green) and sometimes spots or blotches present colored 59B and 60B (red-purple). Lower one-third: 137C (green). Rear surface: Upper two-thirds: 154D (yellow-green) and 11D (yellow) and sometimes spots or blotches present colored 59B and 60B (red-purple). Lower one third: 137C and 137D (green).

*Spadix*.—Length, entire spadix: Average 8.3 cm. Shape: Spindle-shaped to columnar. Apex: Obtuse. Base: Obtuse. Aspect: Upright. Male flower zone: Length: Average 3.9 cm. Diameter: Average 8.6 mm. Color, mature: 158B and 158C (yellow-white). Male flowers: Quantity per spadix: Average 147. Shape: Obovate. Height: Average 2.4 mm. Diameter: Average 2.8 mm. Anther color: 12D (yellow) and 158A (yellow-white). Pollen amount: Moderate. Sterile flower zone: Length: Average 2.8 cm. Diameter: Average 5.0 mm. Color, mature: 159C (orange-white) and 158B (yellow-white). Female flower zone: Length: Average 1.6 cm. Diameter: Average 8.0 mm. Color: 12D (yellow) and 158A (yellow-white). Female flowers: Quantity per spadix: Average 206. Shape: Obovate. Height: Average 2.1 mm. Diameter: Average 1.6 mm. Stigma color: 12D (yellow) and 158B (yellow-white). Ovary color: 12C (yellow) and 158B (yellow-white).

*Scape*.—Length: Average 24.4 cm. Diameter: Average 6.1 mm. Strength: Sturdy and flexible. Aspect: Erect. Texture: Smooth, glabrous. Color: 202A (black) to 200A (brown) with streaks of 201A and 201D (grey) with 200B (brown) and 66A (greyed orange) just below the spathe.

Seeds and fruit.—Seed and fruit development have not been observed.

Disease and pest resistance:

*Fusarium tuber rot*.—Observed to be moderately resistant to *Fusarium* tuber rot that was artificially induced by injecting a spore suspension of three pathogenic *Fusarium solani* isolates into the inside tissue of 'UF-15-131' tubers.

*Pythium root rot*.—Observed to be resistant to *Pythium* root rot that was artificially induced by inoculating a spore suspension of three pathogenic *Pythium myriotylum* isolates into the root balls of plants of 'UF-15-131'.

*Root-knot nematode*.—Observed to be moderately resistant to resistant to *Meloidogyne javanica* in greenhouse inoculation trials and moderately resistant to *Meloidogyne arenaria* in field trials.

Temperature tolerance: Plants of 'UF-15-131' have been observed to be tolerant to temperatures ranging from 7° C. to about 40° C.

ADDITIONAL PLANT COMPARISON

'UF-15-131' was compared to the commercial *Caladium* cultivar 'Cranberry Star' (U.S. Plant Pat. No. 20,792) for plant growth, leaf color display, sunburn tolerance, and leaf health in open fields in full sun. The comparison was made in Wimauma, FL in 2021 and 2022. The soil was EauGallie fine sand with about 1% organic matter and a pH between 6.2 and 7.4. In each year, *Caladium* tubers were treated in hot water (50° C.) for 30 minutes, dusted with RootShield® Plus WP, and planted in beds at approximately 15-cm spacing between rows and in rows. Plants were grown using a white plastic-mulched raised-bed system and irrigated and fertilized through two drip tapes buried under the plastic mulch. A commercial liquid fertilizer (5N-0.87P-6.64K) was used, providing 0.454 kg of nitrogen an acre per day. In each year, trial entries were assigned to the field plots in a randomized complete block design with three replicates and 30 tubers per replicate. Each plot was 1.2 square meters.

A scale of 1 to 5 was used to rate *Caladium* plant growth, with 1=very poor (few leaves and lack of vigor), 3=acceptable as garden plant, and 5=excellent (full plants, numerous leaves). A scale of 1 to 5 was used for rating leaf color display, with 1 being very poor (dull or bleached, lack of color display), 3 acceptable, and 5 excellent (bright, very attractive). Sunburn tolerance was evaluated on a scale of 1 to 5, with 1 being very susceptible to sunburn (leaves having numerous sun-damaged areas or holes) and 5 being resistant to sunburn (no visible sun-damaged areas). Leaf health was evaluated on a scale of 1 to 5, with 1 being numerous diseased spots and completely unsightly and 5 being healthy and free of visible leaf spot disease. Evaluations of plant growth, leaf color, sunburn tolerance and leaf health were performed on Jul. 31, 2020, Aug. 21, 2020, Sep. 25, 2020, Aug. 20, 2021, Sep. 22, 2021 and Oct. 13, 2021.

'UF-15-131' received a plant growth rating between 3.2 and 4.0 in the 2021 season (Table 1). However, the plant growth rating in the first two evaluations in the 2020 season were below 3.0 (1.8 or 2.2) due to lack of care as a result of the disruption of the Covid pandemic in spring 2020. Nevertheless, the 'UF-15-131' performed significantly better than 'Cranberry Star' in two out of the six evaluations. Similarly, plants of 'UF-15-131' received a significantly higher leaf color rating and sunburn tolerance rating than 'Cranberry Star' in two out of six evaluations in 2020 and 2021 (Table 1). Leaf health of 'UF-15-131' was much improved over 'Cranberry Star', with the leaf health rating ranging between 2.7 and 4.3, significantly higher than the ratings 'Cranberry Star' received in four out of the six evaluations (Table 1).

As shown in Table 1, plant growth, sunburn tolerance, leaf color and leaf health ratings of 'UF-15-131' are compared to 'Cranberry Star' grown in ground beds in full sun in Wimauma, FL in 2020 and 2021. Values are means of three plots based on whole plot evaluation in each evaluation.

TABLE 1

Plant growth, leaf color, sunburn tolerance, and leaf health ratings

| | Plant Growth Ratings | | | | | |
|---|---|---|---|---|---|---|
| | 2020 | | | 2021 | | |
| Cultivars | July | August | September | August | September | October |
| 'UF-15-131' | 1.8 | 2.2 | 3.7 a | 3.2 | 4.0 | 4.0 a |
| 'Cranberry Star' | 1.8 | 2.0 | 2.4 b | 3.0 | 3.7 | 3.2 b |
| p value | 1.000 | .6667 | .0377 | .6667 | .4226 | .0377 |
| | **Sunburn Tolerance Rating** | | | | | |
| | 2020 | | | 2021 | | |
| Cultivars | July | August | September | August | September | October |
| 'UF-15-131' | 4.3 | 4.3 | 3.9 | 4.2 a | 3.7 | 4.0 a |
| 'Cranberry Star' | 3.5 | 4.0 | 2.8 | 3.0 b | 3.0 | 3.0 b |
| p value | .1989 | .1835 | .1447 | .0198 | .1835 | .0010 |
| | **Leaf Color Rating** | | | | | |
| | 2020 | | | 2021 | | |
| Cultivars | July | August | September | August | September | October |
| 'UF-15-131' | 2.2 | 2.8 | 3.3 | 3.3 | 3.0 a | 3.0 a |
| 'Cranberry Star' | 2.5 | 3.2 | 2.4 | 3.0 | 2.0 b | 2.0 b |
| p value | .1835 | .6667 | .0927 | .1835 | .0010 | .0010 |
| | **Leaf Health Rating** | | | | | |
| | 2020 | | | 2021 | | |
| Cultivars | July | August | September | August | September | October |
| 'UF-15-131' | 4.2 | 4.3 a | 3.8 a | 4.0 | 3.7 a | 2.7 a |
| 'Cranberry Star' | 3.7 | 3.8 b | 1.8 b | 3.0 | 1.3 b | 1.0 b |
| p value | .4226 | .0001 | .0202 | .0742 | .0428 | .0377 |

What is claimed is:

1. A new and distinct cultivar of *Caladium* plant named 'UF-15-131' as illustrated and described herein.

* * * * *